United States Patent [19]

Yokoyama et al.

[11] Patent Number: 5,324,707

[45] Date of Patent: * Jun. 28, 1994

[54] METHOD OF IN VITRO APPLICATION OF BIOREGULATOR COMPOUNDS

[75] Inventors: Henry Yokoyama; James H. Keithly, both of Pasadena, Calif.; Harold W. Gausman, Amarillo, Tex.

[73] Assignees: Tropicana Products, Inc., Bradenton, Fla.; The United States of America as represented by the Secretary of Agriculture, Washington, D.C.

[*] Notice: The portion of the term of this patent subsequent to Mar. 29, 2011 has been disclaimed.

[21] Appl. No.: 954,726

[22] Filed: Sep. 30, 1992

Related U.S. Application Data

[63] Continuation-in-part of Ser. No. 860,413, Mar. 30, 1992, and a continuation-in-part of Ser. No. 954,725, Sep. 30, 1992.

[51] Int. Cl.$^5$ ............................................ H01N 33/08
[52] U.S. Cl. .................... 504/148; 504/326; 71/64.09
[58] Field of Search ................ 504/326, 148; 564/340, 564/346

[56] References Cited

U.S. PATENT DOCUMENTS 4,204,859  5/1980  Yokoyama ........................... 71/121
4,363,188  12/1982  Dastoor ............................... 71/86 X

OTHER PUBLICATIONS

Harold W. Gausman, John D. Burd, Jerry Quisenberry et al. Bio/Technology vol. 3–Mar., 1985.
Henry Yokoyama, Charles DeBenedict, Wan–Jean Hsu et al. Bio/Technology–Mar., 1984.
J. H. Keithly & H. Yokohama et al. Plant Growth Regulation 9: 19–26, 1990 Kluwer Academic Publishers Printed in Netherlands.

H. Yokoyama and J. H. Keithly–ACS Symposium Series No. 405 Quality Factors of Fruits and Vegetables: Chemistry Technology Copyright 1989 by the American Chemical Society.
James H. Keithly, Hideaki Kobayashi and Henry Yokoyama PGRSA Quarterly 1990 18(2):55–61.
Ernest Hayman, Henry Yokoyama and Seth Gold Journal of Agricultural & Food Chemistry, Mar./Apr. 1987, 186–188, by the American Chemical Society.
Ernest P. Hayman and Henry Yokoyama HortScience 25(12): 1614–1615, 1990.
J. H. Keithly, H. Yokoyama and H. Gausman Plant Growth Regulation 9, 127–136, 1990.

(List continued on next page.)

*Primary Examiner*—Richard L. Raymond
*Assistant Examiner*—B. Bembenick
*Attorney, Agent, or Firm*—Kane, Dalsimer, Sullivan, Kurucz, Levy, Eisele & Richard

[57] ABSTRACT

This invention is directed to a method for the in vitro application of bioregulator compounds. When applied to intact plants in bioregulatory amounts, the compounds enhance important plant properties such as sugar content, essential oils, vitamins, proteins, and an overall increase in total biomass. The treated plants exhibit accelerated growth, accelerated fruit ripening, improved color scores of juice products and an accelerated maturation. The bioregulator compounds which comprise the invention enhance these plant properties when applied individually to plants. It has also been discovered that the application of mixtures of such compounds effect a greater than additive result and enhance the aforementioned plant properties to an unpredicted and unexpected degree when compared to known bioregulator agents. The present application discloses the usage of plant bioregulator agents in an in vitro environment.

11 Claims, 1 Drawing Sheet

OTHER PUBLICATIONS

Wan-Jean Hsu, Charles DeBenedict, Steve D. Lee et al. Jrl. of Agricultural & Food Chemisty, Jan./Feb. 1989, 12–14, by the American Chemical Society.

Wan Jean Hsu and Henry Yokoyama Agricultural & Food Chemistry, Jan., 1991, 96–98 by the American Chemical Society.

H. Yokoyama, S. Gold c. DeBenedict and B. Carter Food Technology 40(11) 111–113, Nov. 1986.

Stephen M. Poling, Wan-Jean Hsu and Henry Yokoyama Phytochemistry, vol. 21, No. 3, pp. 601–604, 1982.

Stephen M. Poling, Wan-Jean Hsu and Henry Yokoyama Phytochemistry, vol. 14, pp. 1933–1938 Paragon Press Printed in England, 1975.

Hideaki Kobayashi, James H. Keithly and Henry Yokoyama (J. Japan. Soc. Hort. Sci.) 59(1): 115–119. 1990.

W.-J. Hsu, H. Yokoyama and C. DeBenedict Phytochemistry, vol. 29, No. 8, pp. 2247–2451, 1990 Printed in Great Britain.

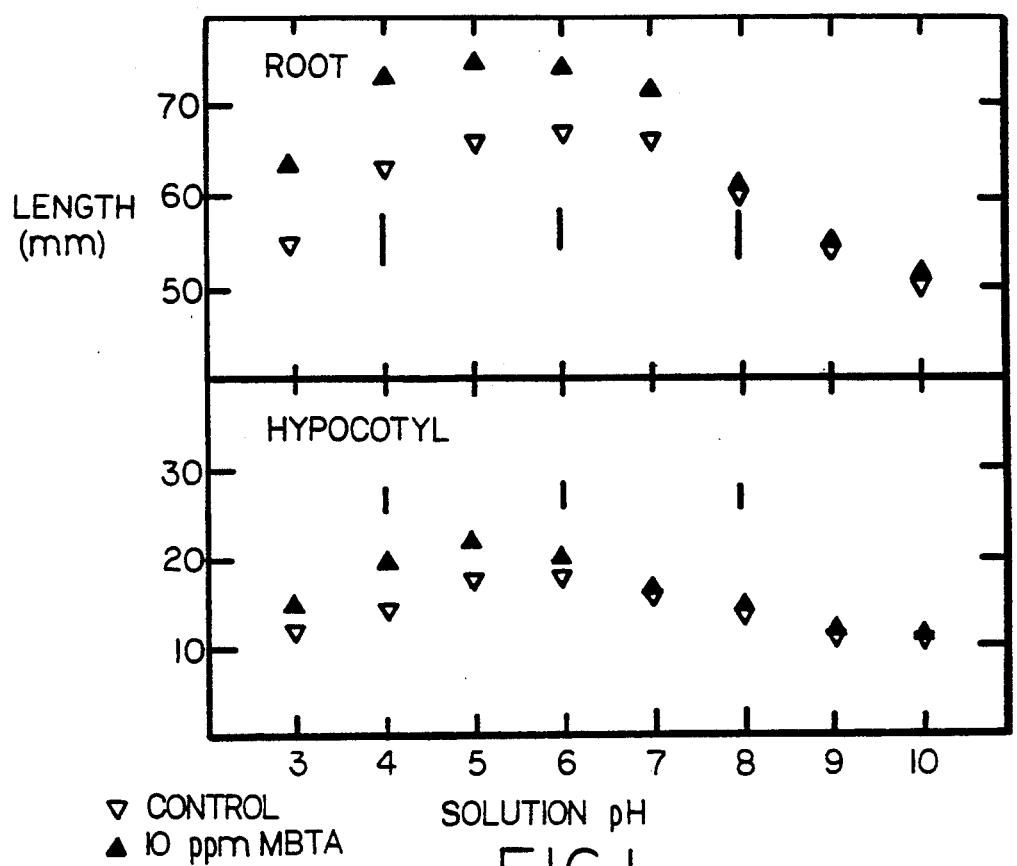
FIG.1
FIG.2
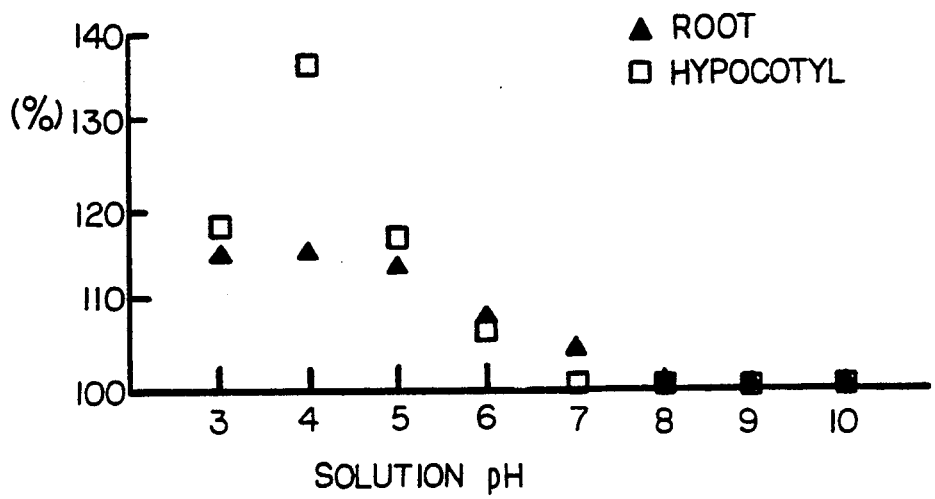

METHOD OF IN VITRO APPLICATION OF BIOREGULATOR COMPOUNDS

This is a continuation-in-part of copending application(s) Ser. No. 07/860,413 filed on Mar. 30, 1992 and a continuation-in-part of copending application Ser. No. 954,725 filed on Sep. 30, 1992.

FIELD OF THE INVENTION

This invention is directed to a method for the in vitro application of bioregulator compounds. When applied to intact plants in bioregulatory amounts, the compounds enhance important plant properties such as sugar content, essential oils, vitamins, proteins, and an overall increase in total biomass. The treated plants exhibit accelerated growth, accelerated fruit ripening, improved color scores of juice products and an accelerated maturation. The bioregulator compounds which comprise the invention enhance these plant properties when applied individually to plants. It has also been discovered that the application of mixtures of such compounds effect a greater than additive result and enhance the aforementioned plant properties to an unpredicted and unexpected degree when compared to known bioregulator agents. The present application discloses the usage of plant bioregulator agents in an in vitro environment.

BACKGROUND OF THE INVENTION

This application is a continuation-in-part of presently pending U.S. application Ser. No. 860,413 filed on Mar. 30, 1992 and a continuation in part of copending application Ser. No. 954,725 filed on Sep. 30, 1992. The disclosures of both of these applications are incorporated herein by reference.

Developments in agriculture have produced chemical compounds and methods for their application which function as plant bioregulators and thus serve to enhance one or more properties of the treated plant. For example, U.S. Pat. No. 3,671,219 discloses a quartenary ammonium compound which when applied to plants enhances the sugar content of sugar cane. U.S. Pat. No. 4,204,859 discloses that the addition of certain phenoxytrialkylamines enhance the hydrocarbon production of rubber in plants. U.S. Pat. No. 4,159,903 discloses a method for increase of polyisoprene production in rubber producing plants such as Guayule. U.S. Pat. No. 3,833,350 discloses that carotenoid accumulation in plants can be increased according to a method comprised by applying compounds including (halogenated phenoxy) trialkylamines. U.S. Pat. Nos. 3,864,501, 3,911,148, and 3,911,152 disclose a method for increasing-the carotenoid pigments of fruits and vegetables which comprises the application of compounds including (methyl phenoxy) trialkylamines.

U.S. Pat. No. 4,797,153 discloses a method for increasing total plant biomass and individual plant constituents such as sugar, protein, lipid, and essential oils which comprises the application of certain substituted phenoxytrialkylamines and substituted phenylthiotrialkyl amines, or dialkylmorpholium halides. The compounds are applied in bioregulatory amounts to plant seeds, plant seedlings, or plant buds at the early stage of plant development, or to trees during a week before or after flower bud swell. It has since been shown that the application of the compounds of this reference in bioregulatory amounts affect the photosynthetic pathway in green plants in a manner which facilitates the assimilation of carbon dioxide in the photosynthetic pathway, thereby increasing the carbon atoms available for synthesis of total biomass and individual plant constituents.

U.S. Pat. No. 4,363,188 discloses a method for the stimulation of the in vitro propagation of Guayule. A substituted trialkyl amine bioinducing agent is introduced into a nutrient medium containing Guayule tissue. Selective or differentiated propagation of shoots or callus is obtained by varying the amounts of substituted trialkyl amine present in the nutrient medium. The Guayule growth, which is described as being luxuriant, can be processed for its polyisoprene content or may be transferred to a rooting medium for production of whole plants that are identical clones of the original tissue. Suitable bioinducing agents are disclosed at columns 5, 6, and 7 of the specification, and include the bioregulator agents disclosed in U.S. Pat. No. 4,797,153. The compounds disclosed in method of the present invention are not disclosed in the '188 patent.

The growth of plants in vitro offers several distinctive advantages over plants grown in their natural environment. Since the in vitro environments are created by individuals the various parameters which constitute the environments such as heat, light, moisture, nutrient content, pH, etc, can be selected so as to best facilitate plant growth. Consequently, the ease in which the environmental parameters can be controlled facilitates research since clinical studies are easily developed and managed. It is a further consequence that certain plants not indigenous to a certain geographical locale can be made available in that region without the need to import them from elsewhere, or that plants can be made available out of season. Furthermore, plants exhibiting superior genetic tendencies can be cloned to produce plants exhibiting the same superior traits. The advantages offered by growth in vitro provide beneficial results to researchers and, commercial growers alike.

SUMMARY OF THE INVENTION

The present invention is directed a method of the in vitro application of the bioregulator compounds disclosed in pending U.S. application Ser. No. 860,413. These bioregulator compounds are (benzyl substituted) trialkylamine ether compounds which when applied to plants in regulatory amounts increase important plant constituents, increase total plant biomass, and increase the rate of plant growth and reduce the time to crop maturity. Pigment accumulation in plant leaves and mature fruits is increased. In citrus crops, the fruits harvested from treated trees exhibit a reduced peel thickness. The compounds are applied to the plants in bioregulatory amounts-that is, an amount sufficient to increase plant biomass and accelerate growth but insufficient to harm the plant. The compounds of the present invention are selected from the group of chemical compounds having the structure:

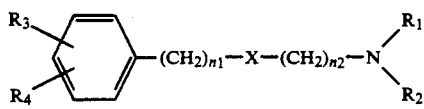

wherein X is either oxygen or sulfur,
$R_1$ and $R_2$ are lower alkyl groups containing 1 to 6 carbon atoms of identical or dissimilar chemical structure, $n_1$ and $n_2$ are integers from 1 to 6, with $n_1$ and $n_2$ being independent of each other, and of identical or dissimilar chemical structure.

$R_3$ and $R_4$ are independently hydrogen, chlorine, fluorine, bromine, iodine, lower alkyl compounds containing 1 to 6 carbon atoms, lower alkoxy compounds containing 1 to 6 carbon atoms, or condensed mono-and polycyclic aromatic ring systems, and wherein:

if $R_3$ and $R_4$ are 3,5-substituents, then the lower alkyl or alkoxy group must contain 3 to 6 carbon atoms; and wherein: if $R_3$ is hydrogen, then $R_4$ must be a 4-substituent, with the proviso that $R_4$ is other than hydrogen; or b) an acid addition salt of the compounds defined above. Mixtures of bioregulator compounds can also be applied to plants. By "mixture" it is intended that the mixture be of at least two compounds selected from the group of chemical compounds having the above disclosed structures.

A second aspect of the invention is the in vitro application of mixtures of the aforedescribed compounds. It has been found that the application of mixtures causes the treated plants to form and store larger quantitites of valuable plant constituents over plants treated with individual bioregulator compounds. The plants which have been treated with the bioregulatory mixtures of the invention have greater biomass than untreated plants resulting in increased crop production per unit area. Moreover, plants treated with these mixtures exhibit enhanced metabolic activity in forming and storing valuable plant constituents and in increasing plant-biomass when compared to plants treated with individual bioregulator agents, which is an unpredicted and unexpected result. The mixtures of the present invention exhibit a greater than additive effect when they are combined as bioregulatory agents and yield synergistic results relative to plants treated with individual bioregulator agents. The inventive mixtures provide a means for optimizing crop production per unit area with respect to the known state of the art.

In our co-pending U.S. application Ser. No. 860,413, it was shown that a compound disclosed therein known as N,N-diethylaminoethyl (4-methylbenzyl) ether (MBTA) is generally more effective as a plant bioregulator than the bioregulator compounds disclosed in U.S. Pat. No. 4,797,153. That is, MBTA treated plants exhibit a greater increase in total plant biomass and valuable plant constituents relative to dichlorophenoxytriethyl amine (DCPTA). A second compound disclosed in our co-pending application, N,N-diethylamine ethyl 3,4-dichlorobenzyl ether (DCBTA) performs comparably as a bioregulator with respect to the DCPTA. We have also discovered that a mixture of DCBTA and MBTA, when applied to plants, effects an unpredicted and unexpected enhancement of plant bioregulatory activity in forming and storing valuable plant constituents and in increasing plant biomass with respect to similar treatments of individual bioregulator agents, including the DCPTA disclosed in U.S. Pat. No. 4,797,153 and the MBTA and DCBTA disclosed in our co-pending application Ser. No. 860,413. The mixture of MBTA and DCBTA, when applied to plants, results in a greater than additive bioregulatory effect when compared to treatments of the aforementioned individual bioregulator agents. Thus, one aspect of the present invention is directed to the in vitro application of DCBTA and MBTA. A second aspect of the present invention is directed towards the in vitro application of a mixture of DCBTA and MBTA.

A particular aspect of the present invention concerns the in vitro application of bioregulator compounds as growth inducing agents on orchid seed germination and germinated orchid seed (protocorm). The propagation of epiphytic orchids requires plant cultivation in vitro. Arditti, J. 1977. Clonal propagation of orchids by means of tisue culture-a manual. In: J. Arditti, (ed), orchid Biology, Reviews and perspectives, pp. 203-293. Cornell Univ. Press, Ithaca, N.Y. Orchid seeds and meristem propagations are cultured on aseptic, artificial media for up to three years before the seedling plants are transferred to greenhouse environments. The greenhouse grown plants are typically cultured for 3 to 5 years to produce mature, blooming plants. The addition of the bioregulator compounds of the present invention an aseptic culture medium significantly enhances orchid protocorm growth.

BRIEF DESCRIPTION OF THE DRAWINGS

FIG. 1 shows the growth of etiolated radish seeds treated with MBTA.

FIG. 2 shows the enhancement of radish growth by MBTA.

DETAILED DESCRIPTION OF THE PREFERRED EMBODIMENT

Any number of isotonic, buffered, nutrient media containing mineral salts as macronutrients and micronutrients, hormones, vitamins and supplements may be utilized in accordance with the present invention so long as they are capable of supporting propagation of the subject plant. For example germination of orchid seeds and orchid protocorm on Hill's seed germination medium, available from Gallup and Sterling Laboratories, Santa Barbara, Calif., was shown to be acceptable. The benefits of the invention are obtained by applying any of the following compounds or mixtures of the following compounds to plant seeds, seedlings or buds. "Mixtures" as used herein, refers to a combination of at least any two compounds encompassed by this disclosure. Examples, by way of illustration and not limitation, of compounds (or mixtures thereof) suitable for use in the method of the invention are:

A. N,N-dialkylaminoalkyl 2,4-substituted benzyl ethers wherein the 2,4-substituents are independently chloro, bromo, iodo, methyl, ethyl, propyl, butyl, pentyl, or isomers thereof, hexyl, methoxy, ethoxy, propoxy, butoxy, pentoxy or hexoxy, and wherein the alkyl and dialkyl groups are independently methyl, ethyl, propyl, butyl or pentyl.

B. N,N-dialkylaminoalkyl 3,5-substituted benzyl ethers wherein the 3,5-substituents are independently chloro, bromo, iodo, methyl, ethyl, propyl, butyl, pentyl, hexyl, propoxy, butoxy, pentoxy or hexoxy, and wherein the alkyl and dialkyl groups are the same as those in A.

C. N,N-dialkylaminoalkyl 3,4-substituted benzyl ethers wherein the 3,4-substituents are independently chloro, bromo, iodo, methyl, ethyl, propyl, butyl, pentyl, hexyl, methoxy, ethoxy, proproxy, butoxy, pentoxy or hexoxy, and wherein the alkyl and dialkyl groups are the same as those in A.

D. N,N-dialkylaminoalkyl 4-substituted benzyl ether wherein the 4-substituent is either methyl, ethyl, propyl, butyl, pentyl, hexyl, methoxy, ethoxy, propoxy, butoxy, pentoxy or hexoxy, and wherein the alkyl and dialkyl groups are the same as those in A.

E. N,N-dialkylaminoalkyl (substituted naphthyl) ether wherein the alkyl and dialkyl groups are the same as those in A.

The preferred compounds of the present invention as set forth in groups A through E are those where $n_1$ is 1 and $n_2$ is 2, X is oxygen, the N,N dialkyl groups are dimethyl, the alkyl group is ethyl, and the benzyl substituents are 2,4-dichloro; 3,4-dichloro; 3-5-diisopropyl; 3,5,-ditertiary butyl; 3,4-dimethyl; 3,4-dimethoxy; 3-methyl, 4-methyl, 4-chloro or 3,4-naphthoxy.

It has been found that a mixture of the compounds DCBTA and MBTA is especially preferred in that plants treated therewith exhibit significant improvements in total plant biomass and individual plant constituents with respect to plants treated with individual bioregulator compounds such as DCPTA, MBTA, and DCBTA. The mixture is further preferably comprised of an equal amount of each of these compounds. However, addition of unequal amounts of two or more bioregulators to an in vitro support medium does not limit the scope of the invention.

Various acid addition salts of the above disclosed compounds are easily produced, and mixtures thereof can be used as well. For example, by adding acid to the compounds of the invention, the following acid addition salts are formed:

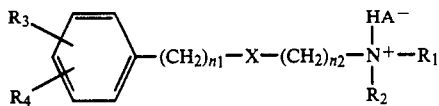

Wherein the molecular constituents are as set forth above, and wherein A is the anion derived from the acid added to the amine to form a salt. Mixtures of acid addition salts are comprised of two or more acid addition salts formed from the above compounds.

In order to achieve increase in total biomass yield, enhancement of individual plant constituents or increase in rate of plant growth, the compounds or mixtures of compounds disclosed above should be introduced into the nutrient media at the earliest stages of plant development. Most preferably, this will be after sterilizaton of the medium and before or contemporaneous with seed or propagule sowing. It should be understood that application of the bioregulators is best made prior to solidification of the agar support. If application is made later some increase in yield or plant constituents may occur but not the significant increase which occurs if treatment is earlier. Since the growth of the plant or propagule dilutes the concentration of the chemical mixture due to increase in plant biomass resulting in a biomass dilution effect, it may be desirable to apply more than one application subsequent to the initial one. Subsequent applications should be made before completion of cell differentiation of the growing plant or when applied to a growing propagule before the completion of cell differentiation of the growing fruit.

The effective amount of the mixture to be applied so as to achieve the increase in biomass contemplated by the invention varies depending upon the stage of the plant's development when application is made, the degree of penetration of the plant by the bioregulator, and whether or not penetrating agents are used.

Generally, where the mixtures are applied to the seeds, application is conveniently made by dissolving the compounds or mixture to be used in water at a concentration of 0.1 to 50 parts per billion (ppb) and introducing the compounds to the sterilized culture medium. It is preferred that if a mixture is used then the mixture can be comprised of equal amounts of each bioregulator agent in the mixture.

Treatment of perennial trees propagated in vitro requires a greater amount of the bioregulator mixture due to the greater mass of the tree. Generally, about 0.01 to 10 mg total active ingredients per tree is applied using a treatment rate of 1 to 100 ppb of bioregulatory mixtures. However, we have found that bioregulatory effects result from applications as low as 0.01 ppb.

Without any intention of limiting the scope of the invention, it is theorized that the compounds comprising the mixtures used in the method of the invention play a role in the photosynthetic pathway in green plants. It is theorized that application of the compounds to the developing green plant causes increased assimilation of carbon dioxide in the photosynthetic pathway thereby increasing the carbon atoms available for synthesis of total biomass and individual plant constituents. It is further theorized that use of the compounds at an early stage of plant or fruit development and before completion of cell differentiation enhances the genetic expression of the plant so as to tap unused biological potential. Thus as new cells develop under the influence of the bioregulatory compounds, they possess increased capacity to form and store valuable materials and to form an increased amount of plant tissues.

As stated above the mixtures of the invention when applied in accordance with the method of the invention, substantially increase total biomass, enhance the amount of some or all plant constituents and in many cases increase the rate of growth in green plants over untreated plants as long as constituents such as water and light which are necessary for plant growth are present in the required amount.

EXAMPLE 1

The propagation of epiphytic orchids requires plant cultivation in vitro. Arditti, J. 1977. Clonal propagation of Orchids by Means of Tissue Culture-A Manual. In: J. Arditti, (ed), Orchid Biology, Reviews and Perspectives, pp. 203-293. Cornell Univ. Press, Ithaca, N.Y. Orchid seeds and meristem propagations are cultured on aseptic, artificial media for up to 3 years before the seedling plants are grown for 3 to 5 years to produce mature, blooming plants. Plant growth rate and seedling vigor during orchid growth in vitro often determine the success and long-term performance of the greenhouse-grown crop. Seedling loss after transfer of the aseptically-grown seedlings to greenhouse culture can also reduce the efficiency of orchid production.

Compared with controls, application of DCPTA to seedling phalaenopsis orchids during routine seedling transfer from aseptic growth in vitro to greenhouse-culture significantly enhanced plant growth and reduced the time to flowering. Keithly, J. H., D. P. Jones and H. Yokoyama, Survival and growth of transplanted orchid seedlings enhanced by DCPTA. HortScience. 26:1284-1286 (1991) (in press, accepted Mar. 12, 1991). In addition, seedling death after transplanting was reduced significantly within the DCPTA treatment groups as compared with controls. Keithly, J. H. and H. Yokoyama, Regulation of plant productivity I: Improved seedling vigor and floral performance of phalaenopsis by 2-(3,4-dichlorophenoxy) triethylamine (DCPTA). Plant Growth Regul. 9:16-26.(1990).

In this example, the growth promoting effects of MBTA, DCBTA, DCPTA, and a mixture of MBTA/DCBTA on seed germination and protocorm development in vitro of Brassolaeliocattleya orchid are examined. Protocorm (germinated seed) development represents the initial growth stage of orchid plant development in vitro. Leaf and root meristems differentiate from the unspecialized protocorm cells to produce a functional orchid seedling.

All orchid seeds were sown on sterilized Hill's seed germination medium obtained from Gallup and Stribling Laboratories, Santa Barbara, Calif. The solid-support medium contained a mixture of buffered mineral salts, auxin, cytokinin, amino acids, organic acids, and agar. The medium (34 g/liter) was solubilized in distilled water and was adjusted to a pH of 5. All orchid cultures were grown in 65×65×100 mm plastic vessels (Magenta Corporation, Chicago, Ill.) that contained 100 ml seed germination medium. All culture vessels were autoclaved for 10 min at 15 psi. After medium sterilization 10 ppb MBTA, 10 ppb DCBTA, 10 ppb DCPTA, and a 10+10 ppb mixture of MBTA and DCBTA were filter-sterilized and were added to the medium (5 ml/vessel) before the agar-support solidified. The bioregulator solutions were prepared in distilled water. Experimental controls received 5 ml aliquots of filter-sterilized water. All treatment groups contained three replicate vessels.

All orchid seed transfers were performed under sterile conditions. Dry seeds of Brassolaeliocattleya X Ruben's Verde (Blc. Green Heart 'Imperial Jade' ×Blc. Lester McDonald 'Kelly' AM/AOS) were surface sterilized for 20 minutes using the hydrogen peroxide (3%, v/v) method disclosed in Snow, R., Improvements in methods for the germination of orchid seeds, Amer. Orchid Soc. Bull. 54:178-181 (1985).

The seeds were then sown, without rinsing, on the bioregulator-amended media. Seeds were distributed evenly on the medium surface with gentle shaking. Seeds were germinated at 23° C. under continuous illumination (75 $\mu E\ m^{-2}\ s^{-1}$) using two wide-spectrum fluorescent lamps.

Days to seed germination were recorded for each bioregulator treatment. Sixty days after seed sowing, protocorms were harvested from each vessel and the total protocorm fresh weight was determined. Fresh weight and diameters for 50 protocorms were determined. Each group of 50 protocorms was extracted into 100% acetone and the chlorophyll and total carotenoids contents were quantified using the spectrophotometric extinction coefficients of Lichtenthaler, H. K., Chlorophylls and carotenoids: Pigments of photosynthetic biomembrances. Methods in Enzymol. 148:350-382 (1987).

Results

Orchid seed germination and protocorm development was enhanced significantly by the addition of tertiary amine bioregulators to the aseptic culture medium (Table 1). During seed sowing, visually equal amounts of seeds were plated into each vessel. Seeds were observed to germinate 13 days after sowing among the control, DCPTA- amended, and DCBTA-amended cultures. However, seeds plated on the MBTA/DCBTA mixture and MBTA-amended cultures were observed to germinate 10 days after seed sowing. Compared with controls, protocorm fresh weight was increased significantly ($P=0.05$) by the addition of bioregulators to the in vitro culture medium (Table 1). Chlorophyll a, chlorophyll b, and total carotenoid contents of mature protocorms grown on tertiary amine bioregulator-amended media (TAB-media) were increased significantly compared with controls. However, the chlorophyll a to b ratios of all treatment groups were statistically similar. Of the compounds that were tested, the MBTA and MBTA/DCBTA mixture treatments showed the largest numerical improvements in protocorm fresh weight and pigment accumulation when compared with controls.

TABLE 1

| Treatment[z] | Protocorm fresh wt (g × 50) | Pigment content (ug/g fresh wt) | | | |
|---|---|---|---|---|---|
| | | Chla | Chlb | Chla/b | Cartot |
| Control | 0.27 d | 57.3 c | 31.7 b | 1.81 a | 32.1 b |
| DCPTA-10 ppb | 0.38 b | 62.5 b | 34.8 ab | 1.80 a | 36.4 ab |
| DCBTA-10 ppb | 0.35 c | 66.1 ab | 35.5 ab | 1.86 a | 38.5 a |
| MBTA-10 ppb | 0.39 b | 69.3 a | 37.8 a | 1.83 a | 41.0 a |
| MBTA/DCBTA- 10 + 10 ppb | 0.43 a | 69.7 a | 38.1 a | 1.83 a | 40.7 a |

[z]DCPTA, N,N-diethylaminoethyl 3,4-dichlorophenylether
DCBTA, N,N-diethylaminoethyl 3,4-dichlorobenzylether
MBTA, N,N-diethylaminoethyl 4-methylbenzylether This study indicates that orchid protocorm growth in vitro is enhanced significantly by the addition of tertiary amine bioregulators to an aseptic culture medium (Table 1). Among the compounds that were tested, treatments that contained MBTA showed the greatest improvements in seed germination, protocorm growth, and total pigment accumulation when compared with controls. The chlorophyll a to b ratios of control and all chemical treatments were numerically similar. These results suggest that chloroplast size (volume) or chloroplast number per cell was enhanced in response to tertiary amine-treatment, rather than a specific enhancement of chlorophyll a or chlorophyll b biosynthesis. These results support earlier studies that showed DCPTA-treatments to enhance the mesophyll chloroplast size of spinach and sugarbeet leaves. In these studies, the total number of chloroplasts per mesophyll cell was not increased by DCPTA-treatment. The potentially enhanced chloroplast size of orchid protocorms grown in TAB-media is significant, since the total chloroplast volume per cell generally determines the photosynthetic carbon fixation rate and cell growth rate of plants. Keithly, J. H., H. Yokoyama and H. W. Gausman, Regulation of crop growth and yield by tertiary amine bioregulators. In: H. W. Gausman, (ed), Plant Biochemical Regulators, pp. 223-246. Marcel Dekker, New York, N.Y. (1991). Pyke, K. A., and R. M. Leech. 1987. Cellular levels of ribulose-1,5-bisphosphate carboxylase and chloroplast compartment size in wheat mesophyll cells. J. Exp. Bot. 38:1949-1956.

EXAMPLE 2

The quaternary ammonium nucleus ($R_4N+$) is an essential structural feature of a wide variety of plant growth regulatory compounds. Schott, P. E. and Walter, H. Bioregulators: Present and Future Fields of Application. In: H. W. Gausman, ed., Plant Biochemical Regulators. Marcel Dekker, New York. pp. 247-321 (1991). Early research studies using DCPTA, MPTA, and CPTA often reported insignificant bioactivity of these compounds on crop plants. In these early studies, the bioregulator solutions were often adjusted to pH 9.0 prior to application to crop plants. Additional protective/complexing agents, such as beta-cyclodextrin, were often added to the bioregulator solutions in an effort to improve the bioactivity of the compounds. Recent studies have shown improved and consistent biological activities of DCPTA when the pH of the working solution (DCPTA+detergent) was adjusted to pH 4 to 5 prior to plant application. This study examines the effect of solution pH on the growth-induction activity of MBTA using a standardized radish seedling growth test.

Radish (Raphanus sativus L. cv. Red devil B) seeds were soaked for 6 hours at 22° C. in solutions that contained: 100 mM Hepes buffer, 10 ppm MBTA, and 0.1% Tween 80 (v/v). Control seed lots were soaked for 6 hours at 22 c in solutions that contained: 100 mM Hepes buffer and 0.1% Tween 80. Individual bioregulator and control solutions were adjusted to pH values 3, 4, 5, 6, 7, 8, 9, and 10 prior to seed incubation. Solution pH values were determined after seed treatment. After treatment, bioregulator solutions were decanted and the seeds were germinated at 27° C. for 48 h in the dark using a standardized ragdoll seed germination method. Keithly, J. H., H. Yokoyama and H. W. Gausman, Promotive effects of DCPTA on seedling development and growth of radish. J. Amer. Soc. Hort. Sci. (in press, 1991).

After 48 hours, primary root and hypocotyl lengths of 50 seedlings were measured. The experiment was performed twice. Significant differences among treatment means were determined by LSD, 5% level.

Results

Seedling growth of control radish seeds was optimized when the ungerminated seeds were hydrated at pH 5 to 7 (FIG. 1). Incubation of seeds in highly acidic (pH of 3) or alkaline (pH>7) solutions significantly inhibited seedling growth of controls. Seedling root growth was enhanced significantly by MBTA when the incubation solutions were adjusted to pH 3 to 6 (FIGS. 1 and 2). Compared with controls, hypocotyl growth was enhanced by MBTA within the test solutions of pH 4 and 5. No growth-enhancement activity of MBTA was observed when radish seeds were incubated in alkaline solutions (FIG. 2). In general, hydration of ungerminated radish seeds in solutions of pH 9 and 10 significantly inhibited seedling growth in control and MBTA seed treatments. FIG. 1 shows the growth of etiolated radish seedlings. Seeds were soaked for 6 h at 22 C in buffered solutions of 1 ppm MBTA that contained 0.1% Tween 80 (v/v). Seeds were germinated in the dark for 48 h using a ragdoll seed germination method.

FIG. 2 shows the enhancement of radish growth by MBTA. Control values were normalized to 100%.

Standardized radish growth tests have proved to be reliable methods to test the growth-enhancing activities of tertiary amine bioregulators. Keithly, J. H., H. Kobayashi, H. Yokoyama and H. W. Gausman, Promotive Effects of Tertiary Amine Bioregulators on Radish (Raphanus sativus) Growth and Development. PGRSA Quarterly 19(3): 182–187 (1991). This study has shown the pH of seed incubation solutions to significantly influence the growth-promoting activity of MBTA (FIGS. 1 and 2). In this study, the external incubation solutions contained a nonionic detergent (Tween 80) and a non-metabolized buffer (Hepes) in order to reduce spurious effects of the incubation solutions upon seedling growth. The use of 100 mM Hepes buffer prevented any significant change in the pH values of the external solutions during seed incubation (data not presented). Alkaline seed incubation solutions clearly negated the bioactivity of MBTA on seedling growth (FIGS. 1 and 2). These results suggest that a quaternary ammonium ($HR_3N+$) structure may be required for tertiary amine bioactivity in plants. Incubation of seeds in pH 3 to 5 solutions may also facilitate the transport of the protonated bioregulator into plant tissues.

These results have several important applications to the successful use of tertiary amine bioregulators in crop plants. Certainly the efficiency of seed soak, cutting soak, and seedling soak-treatments of bioregulator are clearly affected by the pH of the external solution. Keithly, J. H., H. Yokoyama and H. W. Gausman, Regulations of crop growth and yield by tertiary amine bioregulators. In: H. W. Gausman, ed., Plant Biochemical Regulators. Marcel Dekker, New York. pp. 223–246 (1991). In addition, the promotive effects of bioregulator compounds would be greatly influenced by the pH of in vitro cell-culture media. Foliage-treatments may be less affected by solution pH since the amount of solution that is applied per leaf is small, and the treatments are generally performed once during the cycle of plant growth. However, the pH value of the external solution may affect the efficiency of chemical transport into plant tissues.

I claim:

1. A method for the in vitro propagation of plant life from a nutrient medium containing plant life at its early stages of development comprising the steps of:

adding to the nutrient medium an effective amount of at least one bioregulatory agent for plants exhibiting the following chemical structure:

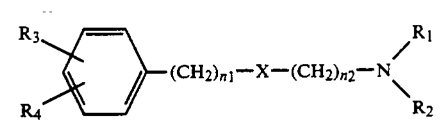

wherein

X is either oxygen or sulfur, $R_1$ and $R_2$ are lower alkyl compounds containing 1 to 6 carbon atoms, $n_1$ and $n_2$ being integers from 1 to 6, $n_1$ and $n_2$ being independent of each other; $R_1$, $R_2$, $n_1$, $n_2$ may be of identical or dissimilar chemical structure;

$R_3$ and $R_4$ are independently hydrogen, chlorine, fluorine, bromine, iodine, lower alkyl compounds containing 1 to 6 carbon atoms, lower alkoxy compounds containing 1 to 6 carbon atoms, or condensed mono and polycyclic aromatic ring systems, and wherein:

if $R_3$ and $R_4$ are 3,5,-substituents, then the lower alkyl or alkoxy group must contain 3 to 6 carbon atoms; and wherein:

if $R_3$ is hydrogen, then $R_4$ must be a 4-substituent, with the proviso that $R_4$ is other than hydrogen.

2. The method as set forth in claim 1 wherein the bioregulatory agent is N,N-diethylaminoethyl 3,4-dichlorobenzyl ether.

3. The method as set forth in claim 1 wherein the bioregulatory agent is N,N-diethylaminoethyl 4-methylbenzyl ether.

4. The method as set forth in claim 1 wherein the bioregulatory agent is a mixture of N,N-diethylaminoethyl 3,4-dichlorobenzyl ether and N,N-diethylaminoethyl 4-methylbenzyl ether.

5. The method as set forth in claim 1 wherein the bioregulator agent is added in a concentration of 0.1 to 50 ppb.

6. The method as set forth in claim 1 wherein the plant life propagated in vitro is derived from: an annual or perennial agronomic crop plant, a woody plant tissue, or from a plant grown for ornamental purposes.

7. The method as set forth in claim 1 wherein the plant life cultured in vitro is obtained from a unicellular or multicellular algal species, of types that may be cultured using liquid or solid in vitro support media.

8. The method as set forth in claim 1 wherein the plant life cultured in vitro is obtained from vegetative or reproductive plant cells or derived from micro-propagated cell lines thereof.

9. The method as set forth in claim 1 wherein the nutrient medium is comprised of a mixture of sugars, amino acides, peptones, organic acids, vitamins, salts, hormones, and/or cell extratives necessary to sustain plant life and cell growth in vitro.

10. The method as set forth in claim 9 wherein the nutrient medium is a liquid.

11. The method as set forth in claim 9 wherein the nutrient medium is a solid that is further comprised of a suitable gelling agent.

* * * * *